United States Patent [19]

Maynor et al.

[11] Patent Number: 5,450,753
[45] Date of Patent: Sep. 19, 1995

[54] METHOD AND APPARATUS FOR COOLING SENSORS IN HIGH TEMPERATURE ENVIRONMENTS

[75] Inventors: John W. Maynor; Stephen E. Smith, both of Arlington; Robert N. Hancock, Bedford, all of Tex.

[73] Assignee: Vought Aircraft Company, Dallas, Tex.

[21] Appl. No.: 990,218

[22] Filed: Dec. 14, 1992

[51] Int. Cl.$^6$ .................................................. G01N 29/28
[52] U.S. Cl. ..................................................... 73/644
[58] Field of Search ........................... 73/570, 505, 644

[56] References Cited

U.S. PATENT DOCUMENTS

| | | | |
|---|---|---|---|
| 4,175,442 | 11/1979 | Terry | 73/644 |
| 4,295,373 | 10/1981 | Moffatt | 73/505 |
| 4,483,195 | 11/1984 | Brown | 73/644 |
| 5,054,321 | 10/1991 | Horvath | 73/644 |

*Primary Examiner*—Hezron E. Williams
*Assistant Examiner*—Christine K. Oda
*Attorney, Agent, or Firm*—Arnold, White & Durkee

[57] ABSTRACT

Sensor assemblies, comprising one or more sensors for use in high-temperature environments such as an aircraft wing, include a thermally conductive retaining member in thermal communication with either the sensor or the environment surrounding the sensor. A housing assembly placed proximate to, and in thermal communication with, the retaining member defines a fluid passageway. During operation, fluid circulates through the housing to enhance the transfer of heat away from the sensor. Such heat transfer facilitates maintaining a sensor environment within the tolerance range of the sensor, thereby facilitating monitoring of the pressure fluctuation (or other sensor parameter) during operation of the aircraft.

7 Claims, 3 Drawing Sheets

METHOD AND APPARATUS FOR COOLING SENSORS IN HIGH TEMPERATURE ENVIRONMENTS

The U.S. Government has a paid-up license in this invention and the right in limited circumstances to require the patent owner to license others o reasonable terms as provided for by the terms of Contract No. F33657-81-C-0067 awarded by the U.S. Air Force, and Subcontract No. 367-197300-AK, between Northrop Grumman Corporation and Vought Aircraft Company.

BACKGROUND OF THE INVENTION

The present invention relates generally to methods and apparatus for cooling sensors located in areas in which the sensors are subjected to temperature extremes, and more specifically relates to such methods and apparatus believed to have particular utility relative to sensors mounted in extreme temperature environments on aircraft.

In the design and evaluation of various types of equipment, such as, for example, aircraft (planes, missles, etc.); sensors, such as temperature sensors (or thermocouples), strain gauges, and fluctuating pressure or acoustic sensors may be placed upon an aircraft, such as either a prototype or a production aircraft, to evaluate actual conditions to which portions of the aircraft are subjected. This facilitates evaluation of the actual design relative to the conditions anticipated during the design process. For example, portions of an aircraft in the vicinity of the engine exhaust may be evaluated with thermocouples and acoustic sensors to determine the temperature and pressure or vibration to which the portions are subjected during operation of the aircraft. Such evaluation facilitates assuring the viability of the design.

A particular problem in this regard has been presented relative to certain sensors, such as acoustic sensors (generally known as "microphones") utilized in such an environment. In some applications, these acoustic sensors may be subjected to exceptional temperature loading; for example, 800 degrees fahrenheit or higher. In many cases, the temperature loading may exceed the normal thermal tolerance of the microphone or sensor. For example, microphones utilized for such tests typically have a thermal tolerance of approximately 500 degrees fahrenheit or less. As acoustic sensors utilized for such purposes are typically quite expensive, often costing several hundreds of dollars, the risk of damaging sensors through excessive heat loading in the environment in which they are placed has presented a significant and expensive problem in aircraft evaluation operations.

Additonally, sensors adapted for extreme high temperature environments typically use extremely expensive sensors, often costing on the orders of tens of thousands of dollars, but which exhibit a significant reduction in sensitivity. Accordingly, generally, the lower temperature environment that an acoustic sensor may be designed for, than a greater sensitivity may be maintained in the sensor.

Accordingly, the present invention provides a new method and apparatus for facilitating the placement of sensors, such as acoustic sensors in high temperature environments. The present invention also facilitates the use in high temperature environments of acoustic sensors having optimal sensitivity for the application in question.

SUMMARY OF THE INVENTION

The present invention provides a sensor assembly particularly useful in monitoring at least one parameter or condition proximate the surface of an aircraft. The assembly includes at least one sensor, which in at least one particularly preferred embodiment will be an acoustic sensor, such as a microphone. The sensor will preferably be retained within a retaining member which will preferably be in thermal communication with the sensor, or at least with the environment surrounding the sensor. In one particularly preferred embodiment, the retaining member will be cooperatively conformed with the surface of the aircraft to facilitate an upper portion of the retaining member lying in essentially flush relation relative to the aircraft surface, with a securing portion of the retaining member extending through the aircraft surface.

In one particularly preferred implementation of the present invention, the retaining member will provide the structure for retaining the sensor and the assembly, and the retaining member will have associated with it a housing defining a fluid path or conduit. A source of fluid will then be provided through which fluid may be communicated to the housing. In a presently envisioned embodiment, a plurality of sensors may be included proximate at least a portion of an aircraft surface, and each sensor will be in fluid communication, either directly or through another housing assembly, with the fluid inlet. Additionally, each sensor will preferably be in fluid communication, either directly or indirectly, with a fluid outlet.

In operation, the circulating of fluid through the housing facilitates the transfer of heat away from the sensor. Such heat transfer thus facilitates maintaining a sensor environment within the tolerance range of the sensor, thereby facilitating monitoring of the pressure fluctuation (or other sensor parameter) during operation of the aircraft.

DETAILED DESCRIPTION OF PREFERRED EMBODIMENTS

Figure 1:
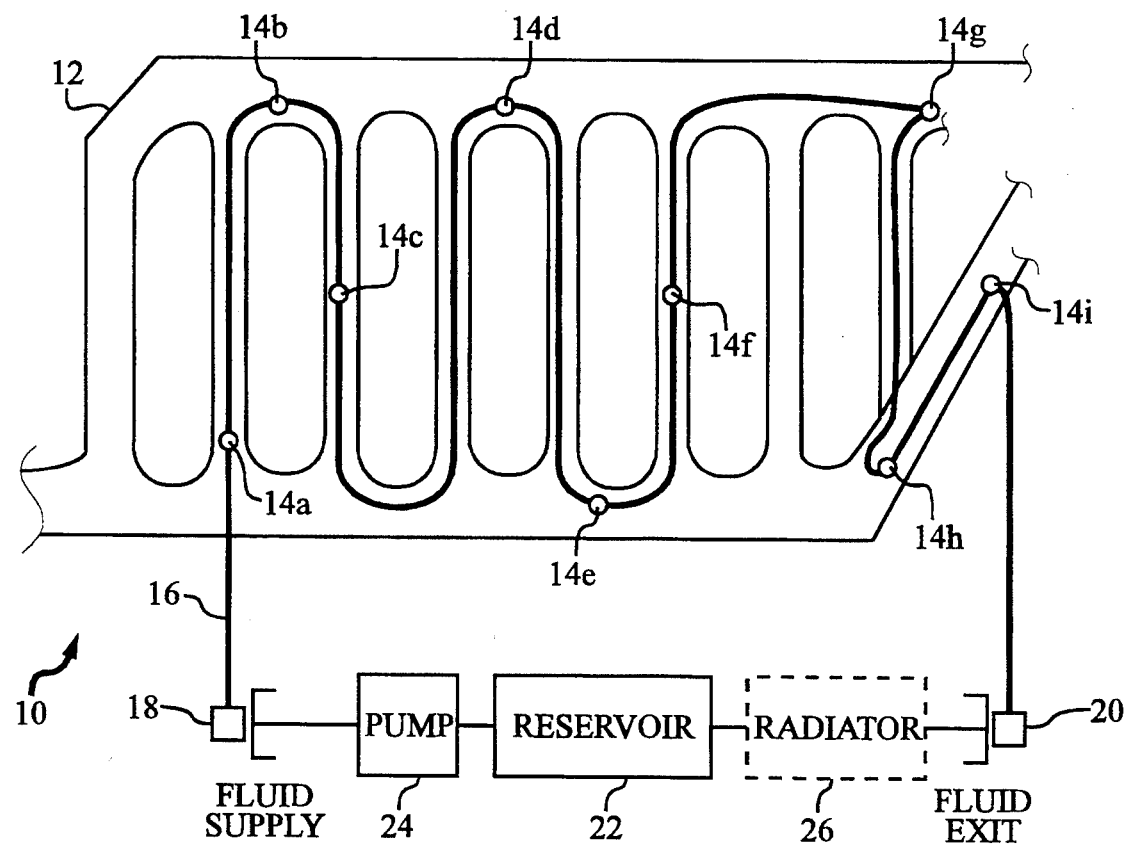
FIG. 1 depicts an exemplary sensor cooling system in accordance with the present invention.

Referring now to the drawings in more detail, and particularly to FIG. 1, therein is illustrated an improved sensor array 10 in accordance with the present invention. Sensor array 10 is depicted, by way of example only, in relation to a structural frame assembly 12 of a type as might be utilized to support a surface of an aircraft; one exemplary environment in which the present invention is believed to have particular utility. Sensor array 10 includes a plurality of individual sensor installations 14a-i. Each sensor installation will be described in more detail in reference to FIG. 2.

Each sensor installation 14a-i in accordance with the present invention includes a fluid-carrying jacket or housing cooperatively arranged with a sensor mounting to facilitate heat transfer from the mounting to the fluid.

In one preferred implementation, as depicted, a conduit assembly, indicated generally at 16, will extend from a fluid inlet 18 to interconnect each sensor installation 14a–14i in series, and to communicate with a fluid outlet 20. Alternatively, the fluid inlet 18 and outlet 20 may be manifolded to place one or more sensor installations 14 directly in fluid communication with fluid inlet 18 and fluid outlet 20. The selected fluid may be chosen according to a particular application. Where sensor installations 14a–14i will be mounted on a surface which will remain relatively fixed, fluid may be circulated through conduit assembly 16 in virtually any desired manner. For example, in one test configuration, where a sensor array has been disposed within a portion of an aircraft, but where the aircraft was to remain substantially stationary during the test, conventional tap water has been circulated from a fluid inlet 18 through a conduit assembly 16, and to a fluid exit 20. In this implementation, the fluid supply constituted, at its origin, connection to a conventional tap water supply, and the fluid outlet was a conduit to allow the water to merely exit the aircraft and pass to the ground. Additionally, the signal to noise ratio from the sensors was on the order of approximately 30–40 db; in significantly improved contrast relative to that which might be expected with less sensitive sensors combined to withstand the 600 degrees plus environment.

In an alternative configuration, where the structural member to which the sensor array is coupled is not intended to remain stationary, a transportable system could be provided, as indicated between brackets, in FIG. 1. In such an exemplary system, fluid inlet 18 may be coupled to a fluid supply, such as a fluid reservoir 22. Depending upon the application, fluid may be circulated through gravity, or a pump 24 may be placed in fluid communication with reservoir 22 to facilitate the providing of fluid to fluid inlet 18. Depending upon the heat to be removed from the fluid, and the environment in which the system will be utilized, it may also be desirable to include a radiator 26 (depicted in dash lines), or similar heat transfer member to facilitate cooling of the fluid prior to recirculation past sensor installations 14.

Figure 2:
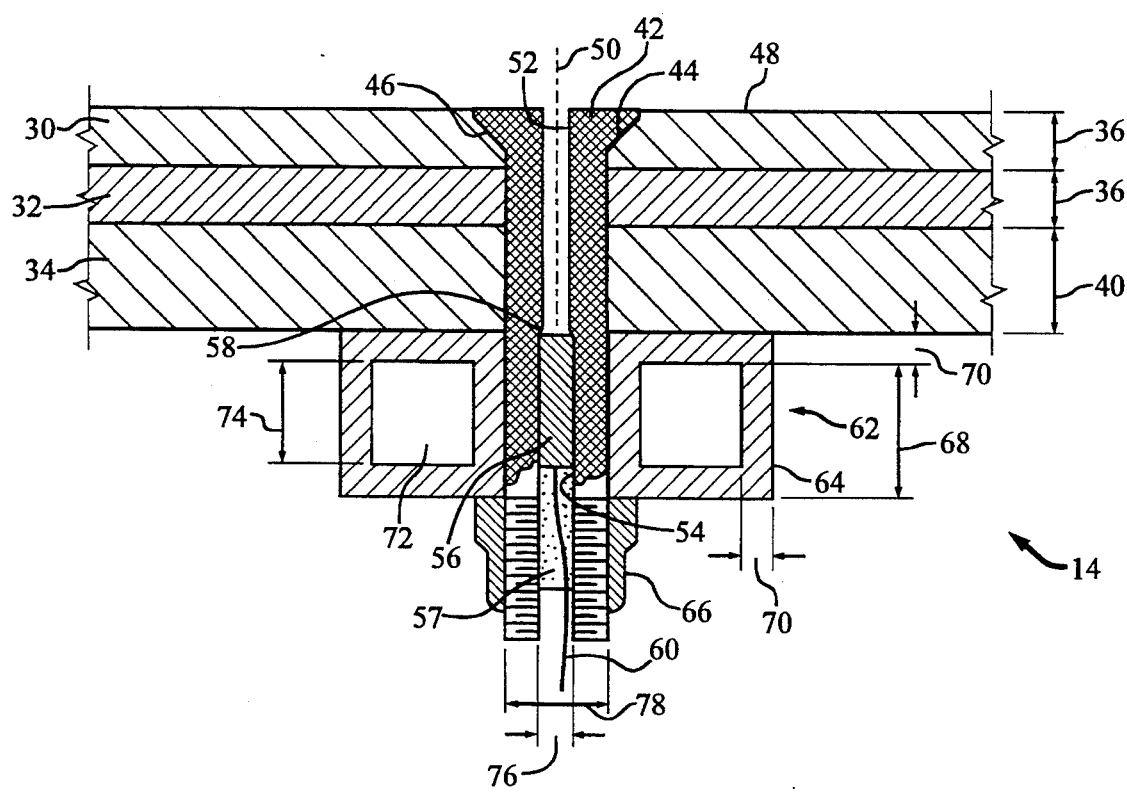
FIG. 2 depicts an exemplary individual sensor installation of the apparatus of FIG. 1, depicted partially in vertical section.
Figure 3:
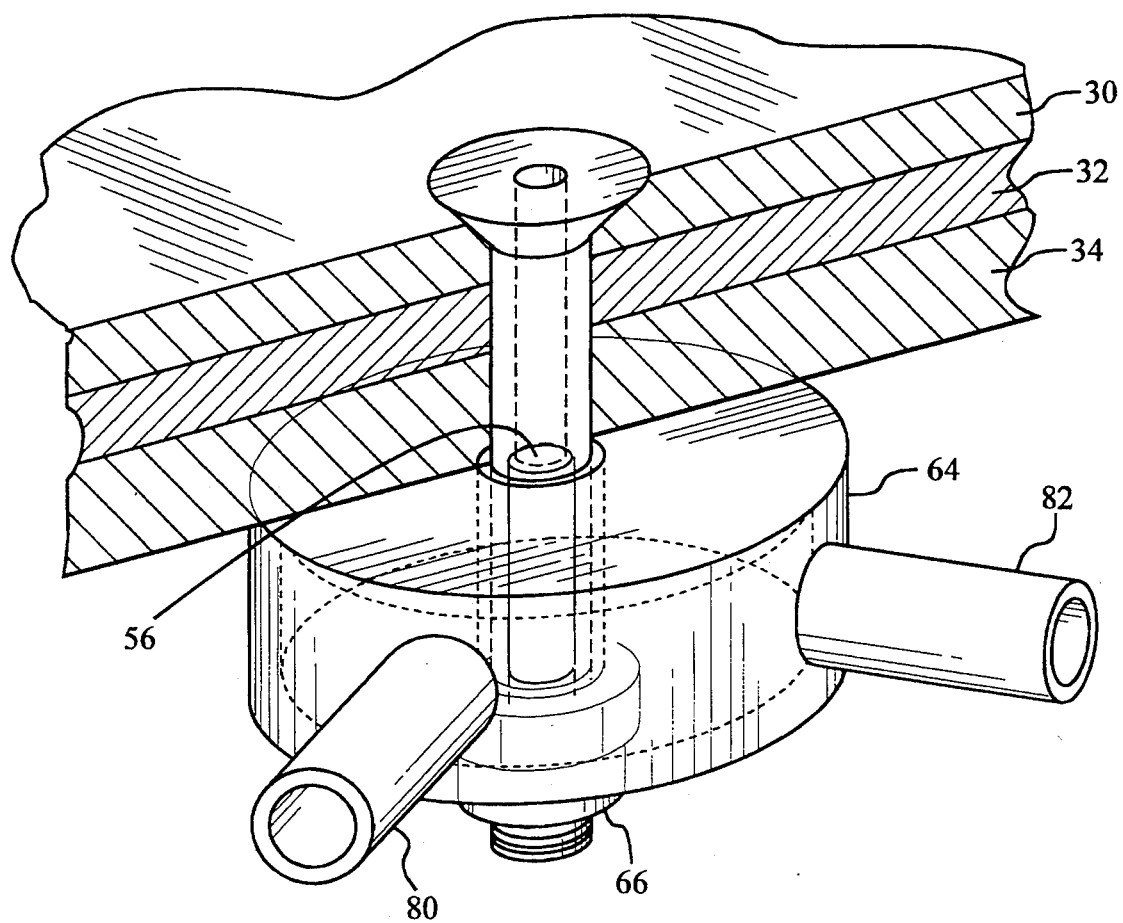
FIG. 3 depicts an exemplary sensor cooling system, illustrated in part from an external oblique view.

Referring now to FIGS. 2 and 3, therein is depicted, from two views, an exemplary sensor installation 14 in accordance with the present invention. Sensor installation 14 is depicted in one exemplary configuration disposed against a surface construction as might be encountered at an aircraft surface formed of a composite structure. Therein is depicted a composite material skin 30 secured on a substrate 32. Skin 30 and substrate 32 may also be affixed to the upper bead of a structural element 34. By way of example, skin 30 might be expected to have a thickness 36 of approximately 0.160 inches, as would substrate 32; while bead 34 might have a thickness 40 of approximately 0.260 inches.

A mounting pin 42 includes a taper 44 adapted to seat within a chamber 46 to provide a flush mounting relative to upper surface 48 of skin 30. Mounting pin 42 includes a securing portion having a generally longitudinal bore 50 having a first portion 52 longitudinally disposed relative to a second, preferably relatively enlarged, portion 54. The sensor 56 is preferably disposed within second portion 54 of longitudinal bore 50 and seats against a shoulder 58 formed at the transition from first portion 52 to second portion 54. Sensor 56 may be retained in second portion 54 by filling the extent of lower portion 54 beneath sensor 56 with an appropriate retaining element, such as a high temperature silicon adhesive 57. Silicon adhesive 57 will facilitate the passing of wires 60 providing electrical communication from sensor 56 while providing mechanical retention of sensor 56 within longitudinal bore 50.

Disposed generally concentrically to mounting pin 42 is a cooling jacket assembly 62. Cooling jacket assembly 62 includes a housing 64 which fits closely around the exterior of mounting pin 42 beneath bead 34. In one particularly preferred embodiment, both mounting pin 42 and housing 64 will be formed of an appropriate heat conducting material, such as stainless steel. Such material establishes thermal communication from sensor 56 and the environment surrounding sensor 56 both to mounting pin 42, and through mounting pin 42 and housing 64 to a fluid within housing 64. Housing 64 is retained in position relative to mounting pin 42 by a securing nut 66, which also retains mounting pin 42 in flush-mounted position relative to skin 30. Securing nut 66 merely threadably couples to mounting pin 42. In one exemplary embodiment, housing 64 will have a vertical dimension 68 of approximately 0.75 inches with a wall thickness 70 of approximately 0.10 inch, defining a central fluid channel 72 having a dimension 74 of approximately 0.550 inch. Also in this exemplary embodiment, lower portion 54 of central longitudinal bore 50 of mounting pin 42 might be expected to have a diameter 76 of approximately 0.100 inch, while mounting pin 42 would have an exterior diameter 78 of approximately 0.250 inch. Housing 64 will preferably have a generally cylindrical exterior construction, and will also thereby preferably define a generally cylindrical fluid channel 72. As will be evident from a review of FIG. 1, fluid inlet and outlet fittings will be secured to housing 64 to establish fluid communication from exterior to housing 64 with fluid channel 72. In one preferred embodiment, housing 64 will be of generally circular form, and will therefore form a generally toroidal member defining fluid channel 72. In this embodiment, a fluid inlet 80 and a fluid outlet 82 will preferably be at relatively radially displaced positions relative to housing 64.

In one preferred installation, the housing 64 of each sensor installation 14 will be connected with an appropriate conduit, such as tubing having an appropriate diameter and temperature tolerance. For example, 5/16 inch tubing formed of Tygon has been found to be suitable for this purpose.

The embodiment depicted in FIGS. 2 and 3 is particularly useful for retaining an acoustic sensor such as a microphone. In one test application wherein sensor installations were intended to withstand temperatures of up to at least 800 degrees fahrenheit, Model XCE-093 microphones manufactured by Kulite Semiconductor Products, Inc. of Leonia, N.J., were successfully utilized. As can be seen in the depicted embodiment, the upper surface of sensor (or microphone) 56 is approximately 0.580 inch beneath upper surface 48 of skin 30. Also in this exemplary embodiment, upper portion 52 of central bore 50 of retaining pin 42 has a bore of approximately 0.075 inch. Those skilled in the art will recognize that the diameter and depth of first portion 52 relative to the frequency response characteristics of an acoustic sensor will be an important consideration. The preferred dimensions of upper portion 52 may be determined in accordance with techniques well-known to those skilled in the art, and will be determined in response to the specific microphone being utilized and the anticipated frequencies being examined.

In operation of one test implementation of the invention, an aircraft surface was tested was tested wherein ambient conditions proximate the sensors in excess of 600 degrees fahrenheit. During the test, tap water was circulated once through manifolding connecting end sensor installation to a fluid inlet and outlet. The water was circulated at a rate of approximately 1 pint per minute. This rate of water under ambient conditions was sufficient to establish temperature conditions satisfactory to maintain functioning of each sensor during the test.

Many modifications and variations may be made in the techniques and structures described and illustrated herein without departing from the spirit and scope of the present invention. For example, the dimensions of each fluid chamber surrounding each sensor may be adapted for a specific environment. Additionally, while chambers defining toroidal fluid cavities around each sensor have been described, those skilled in the art will recognize that many alternative constructions might also be utilized. Additionally, although the system has been described as utilizing water as a fluid medium, other fluids could be utilized. Accordingly, it should be readily understood that the techniques and structures described and illustrated herein are illustrative only and are not to be considered as limitations upon the scope of the present invention.

What is claimed is:

1. A sensor assembly for monitoring at least one condition proximate a surface of an aircraft, said sensor assembly comprising:
    a plurality of sensors;
    at least one retaining member having at least one of said plurality of sensors retained therein, said at least one retaining member having an upper surface cooperatively configured with said surface of said aircraft to lie proximate said surface of said aircraft and further having a securing portion extending from said retaining member's surface through at least a portion of said surface of said aircraft; and at least one fluid chamber cooperatively arranged proximate said at least one retaining member to establish thermal communication between said plurality of sensors in said at least one retaining member and a fluid within said at least one fluid chamber to control the temperature environment of said plurality of sensors.

2. The sensor assembly of claim 1, wherein said at least one retaining member has a generally cylindrical body portion, and wherein said at least one fluid chamber is defined by a housing, and wherein each said body portion of said retaining member extends through a portion of said housing of an associated fluid chamber.

3. The sensor assembly of claim 1, wherein said plurality of sensors comprises at least one acoustic sensor.

4. A sensor assembly for monitoring at least one condition proximate a surface of an aircraft, comprising:
    a retaining member, said retaining member having an upper surface configured to lie proximate the surface of said aircraft, and having a securing portion configured to extend through at least a portion of the surface of said aircraft, said retaining member comprising a bore therein;
    a sensor, said sensor retained at least partially within said bore of said retaining member;
    a fluid housing, said fluid housing configured to extend around said securing portion of said retaining member and to establish thermal communication therebetween, said fluid housing comprising a fluid passage; and
    a securing member adapted to secure said retaining member to said aircraft surface and to secure said fluid housing proximate said retaining member.

5. The sensor assembly of claim 4, wherein said retaining member is formed at least partially of metal, and wherein said fluid housing is formed at least partially of metal.

6. The sensor assembly of claim 4, wherein said sensor comprises an acoustic sensor.

7. The sensor assembly of claim 4, further comprising a volume of fluid passed through said housing.

* * * * *